(12) United States Patent
Desrosiers et al.

(10) Patent No.: US 7,597,852 B2
(45) Date of Patent: Oct. 6, 2009

(54) SUBSTRATE FOR SAMPLE ANALYSES

(75) Inventors: Peter J. Desrosiers, Santa Clara, CA (US); Matthew F. Smith, San Jose, CA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 754 days.

(21) Appl. No.: 11/219,445

(22) Filed: Sep. 2, 2005

(65) Prior Publication Data

US 2006/0051251 A1    Mar. 9, 2006

Related U.S. Application Data

(60) Provisional application No. 60/607,208, filed on Sep. 3, 2004.

(51) Int. Cl.
*B01L 3/00* (2006.01)
(52) U.S. Cl. .............. 422/102; 422/58; 422/82.09; 436/164; 436/165; 250/428; 356/246
(58) Field of Classification Search ............ 422/58, 422/82.09, 102; 436/164, 165
See application file for complete search history.

(56) References Cited

U.S. PATENT DOCUMENTS

| 4,675,889 | A |  | 6/1987 | Wood ........................ 378/84 |
| 5,022,064 | A |  | 6/1991 | Iketaki ...................... 378/145 |
| 5,776,359 | A |  | 7/1998 | Schultz et al. ............ 252/62.51 |
| 6,157,449 | A |  | 12/2000 | Hajduk ...................... 356/367 |
| 6,371,640 | B1 |  | 4/2002 | Hajduk et al. .............. 378/208 |
| 6,373,570 | B1 |  | 4/2002 | McFarland et al. .......... 356/364 |
| 6,536,944 | B1 |  | 3/2003 | Archibald et al. ............ 374/20 |
| 6,664,067 | B1 |  | 12/2003 | Hajduk et al. ............... 435/7.1 |
| 6,679,130 | B2 |  | 1/2004 | Hajduk et al. ............... 73/866 |
| 6,680,996 | B2 |  | 1/2004 | Yokhin ...................... 378/70 |
| 6,936,471 | B2 |  | 8/2005 | Hajduk et al. ................ 436/2 |
| 7,018,838 | B2 | * | 3/2006 | Murphy et al. ............. 435/325 |
| 2003/0124028 | A1 |  | 7/2003 | Carlson ...................... 422/68.1 |
| 2003/0153089 | A1 |  | 8/2003 | Kuil .......................... 436/164 |

FOREIGN PATENT DOCUMENTS

| CA |  2 344 755 | 11/2004 |
| WO | WO 02/06802 | 1/2002 |
| WO | WO 03/031959 | 4/2003 |
| WO | WO 03/060497 | 7/2003 |

* cited by examiner

*Primary Examiner*—Jill Warden
*Assistant Examiner*—Dwan A Gerido
(74) *Attorney, Agent, or Firm*—Senniger Powers LLP

(57) ABSTRACT

Apparatus and methods for screening a library of materials. Materials are provided in a plurality of locations on a substrate. The locations include first regions that are sufficiently transparent to a first form of radiation to permit analysis of the portion of the sample material supported in the first region using a first analytical technique, and second regions that are sufficiently transparent to a second form of radiation to permit analysis of a portion of the sample supported in the second region using a second analytical technique, but are insufficiently transparent to the first form of radiation to permit analysis of the portion of the sample material supported in the second region using the first analytical technique. Sample materials are screened at one or more sample locations of the substrate using the first analytical technique in the first region and the second analytical technique in the second region.

38 Claims, 6 Drawing Sheets

SUBSTRATE FOR SAMPLE ANALYSES

CLAIM OF PRIORITY

The present invention claims the benefit of the priority of U.S. Provisional Application Ser. No. 60/607,208, filed Sep. 3, 2004, the contents of which is incorporated herein by reference for all purposes.

BACKGROUND

This invention relates to methods and apparatus for rapidly screening materials, and in particular to the combinatorial preparation and screening of diverse libraries of materials using transmission X-ray diffraction and other screening techniques.

One approach to the discovery of new materials involves the generation of large collections (libraries) of materials and the systematic screening of those collections for materials having a desired property. Given approximately 100 elements in the periodic table that can be used to make compositions consisting of two or more elements, an incredibly large number of possible new compounds remains largely unexplored. As such, there is a need for more efficient, economical and systematic approach for the synthesis of novel materials and for the screening of such materials for useful properties.

In general, combinatorial material science refers to methods for creating a collection of chemically diverse compounds or materials and to methods for rapidly testing or screening this library of compounds or materials for desirable characteristics or properties. The combinatorial technique, which was introduced to the pharmaceutical industry in the late 1980s, has dramatically sped up the drug discovery process. Recently, combinatorial techniques have been applied to the synthesis of inorganic materials. Using various surface deposition techniques, masking strategies or processing conditions, it is possible to generate hundreds or thousands of materials with distinct compositions per square inch in an array of elements which form a library. The materials generated using these combinatorial techniques have included high temperature superconductors, magnetoresistors, phosphors and pigments. The discovery of new catalysts should also benefit from these combinatorial techniques. General combinatorial material science methodologies are disclosed, for example, in U.S. Pat. No. 5,776,359, which is incorporated by reference herein.

Once these libraries of hundreds or thousands of new potential materials have been generated, they must be screened for performance characteristics or properties. The potentially vast number of materials to be screened, combined with the often low concentration of components in each library member, places a premium on the need for rapid screening techniques that are able accurately to measure properties at low concentration levels.

In many cases, it can be desirable to screen materials libraries using two or more different screening techniques. Depending on the particular properties to be measured, screening techniques that can be useful in this context may include x-ray diffraction analysis, Raman spectroscopy, infrared spectroscopy, ultraviolet spectroscopy, thermal imaging, electron microscopy, optical microscopy, polarimetry, fluorometry, as well as other known techniques. Examples of the application of such techniques are described in U.S. Pat. Nos. 6,157,449, 6,371,640, 6,373,570, 6,536,944, and U.S. Patent Application Publication No. US2003/0124028, all of which are incorporated by reference herein. However, the application of multiple screens can greatly extend the amount of time required to characterize libraries of materials, particularly as the number of materials grows large. And where material or sample transfer and/or manual handling of the materials is necessary to prepare the materials for each different screen—for example, when different screening techniques have different structural or environmental requirements—the time required to completely screen a large library can grow even more.

SUMMARY

The invention provides apparatus, including substrates and sample holder assemblies, as well as methods of using the same, that are useful in the preparation and screening of materials.

In general, in one aspect, the invention provides substrates for holding samples for analysis. The substrates include a plurality of sample locations, each providing a sample surface for supporting a sample for analysis. Each sample location includes at least two different regions. A first region is adapted for the performance of a first type of analytical measurement upon a sample disposed in or on a given sample location. A second region is adapted for the performance of a second, different type of analytical measurement upon the sample disposed on or on the sample location.

Particular embodiments may include one or more of the following features. The first region can be adapted for performance of the first type of analytical measurement by virtue of one or more substrate properties in the first region, while the second region is adapted for performance of the second type of analytical measurement by virtue of one or more substrate properties that are different than the properties of the first region. The first and/or second regions can be provided such that performance of the second type of analytical measurement in the first region (and/or performance of the first type of analytical measurement in the second region) would be less than optimal—for example, it may be difficult or impossible to usefully perform the second type of analytical measurement in the first region because of one or more properties of the first region (such as the type of material from which the first region is made, the thickness of the material, or the like).

In general, in another aspect, the invention provides apparatus for holding samples for analysis. The apparatus includes a substrate having a surface providing a plurality of sample locations for receiving a plurality of samples. Each of the plurality of sample locations includes a first region and a second region. The first regions are adapted to support a portion of a sample material disposed in the corresponding sample location and are sufficiently transparent or sufficiently non-interfering to a first form of radiation to permit analysis of the portion of the sample material supported in the first region using a first analytical technique. The second regions are adapted to support a portion of the sample material disposed in the corresponding sample location and are insufficiently transparent to the first form of radiation to permit analysis of the portion of the sample material supported in the second region using the first analytical technique.

Particular embodiments can include one or more of the following features. The second regions can be sufficiently transparent or sufficiently non-interfering to a second form of radiation to permit analysis of a portion of the sample supported in the second region using a second analytical technique. The first form of radiation and the second form of radiation can be different forms of radiation selected from the group consisting of x-ray radiation, IR radiation, UV-Vis radiation, and visible radiation. The first analytical technique and the second analytical technique can be independently selected from (1) x-ray diffraction in a transmission geometry, (2) IR spectroscopy, and (3) UV-vis spectroscopy, Raman spectroscopy, fluorometry, polarimetry, or optical microscopy. The substrate surface can be a substantially flat surface, with the plurality of sample locations being provided as separate locations on the substantially flat surface. The substrate can include a plurality of receptacles for receiving the plurality of samples, where each of the plurality of sample locations corresponds to one of the plurality of receptacles. Each of the plurality of sample locations can include two or more second regions, with each of the two or more second regions being adapted to permit analysis of the portion of the sample material supported in the respective second region using a different analytical technique.

The substrate can include segments of a first material adjacent to segments of a second material. The first material can be transparent to the first form of radiation. The second material can be opaque to the first form of radiation. Each of the plurality of sample locations can include at least a portion of one or more of the segments of the first material and at least a portion of one or more of the segments of the second material. The substrate can include a plurality of removeable inserts. Each of the plurality of inserts can provide a sample support surface for a corresponding one of the sample locations and including the first region and the second region of the corresponding sample location. The substrate can include a substrate plate having a first surface and a second surface. The substrate plate can define a plurality of through-holes extending from the first surface to the second surface. Each of the plurality of through-holes can be configured to receive one of the plurality of inserts. Each of the plurality of inserts can include a segment of the first material and a segment of the second material located adjacent to the segment of the first material. Each of the plurality of sample locations can have a sample support surface covering the corresponding portions of the segments of the first material and the second material to provide a uniform surface for receiving the sample materials in the sample locations.

The apparatus can include sample support surface including a layer of material that does not substantially interfere with either the first analytical technique in the first regions or the second analytical technique in the second regions. The first analytical technique can be x-ray diffraction in a transmission geometry, and the sample support surface can be formed from a layer of glass that is sufficiently thin to avoid substantial scattering of x-rays during the transmission x-ray diffraction analysis in the first regions.

The apparatus can include a sealing layer configured to cover the sample locations. The sealing layer can include a plurality of first regions and a plurality of second regions corresponding to the first regions and the second regions of the sample locations defined on the substrate surface. The apparatus can include a substrate block having a first surface and a second surface. The substrate block can include a plurality of through-holes extending from the first surface to the second surface. Each of the plurality of through-holes can correspond to one of the plurality of sample locations. The substrate block can be configured to be releasably coupled to the substrate to form a plurality of sample wells. Each sample well can be formed from one of the sample locations and the corresponding through-hole.

The substrate surface can provide at least 24, 48, 96, 384 or more sample locations. The first regions can be transparent or weakly diffracting to x-ray radiation and comprise a material selected from the group consisting of beryllium, aluminum, polyimide, polyacetate, and polyethylene terephthalate. The second regions can be transparent or weakly diffracting to IR radiation and comprise a material selected from the group consisting of $BaF_2$, $CaF_2$, KBr and sodium chloride. Alternatively, the first regions can be transparent to IR radiation and comprise a material selected from the group consisting of $BaF_2$, $CaF_2$, KBr and sodium chloride. Where the first regions are transparent to x-ray radiation or IR radiation, the second regions can be optically transparent and comprise a material selected from the group consisting of glass, quartz and sapphire. The first regions can be transparent to x-ray radiation and comprise beryllium, and the second regions can be optically transparent, and comprise glass, quartz or sapphire.

In general, in another aspect, the invention provides methods of screening a plurality of materials. The methods include providing a plurality of materials in a corresponding plurality of separate sample locations on a substrate, screening a first one of the plurality of materials at a first sample location of the substrate using a first analytical technique, and screening the first one of the plurality of materials at the first sample location of the substrate using a second analytical technique. Each of the plurality of sample locations includes a first region and a second region. The first regions are adapted to support a portion of the sample material disposed in the corresponding sample location and are sufficiently transparent or sufficiently non-interfering to a first form of radiation to permit analysis of the portion of the sample material supported in the first region using the first analytical technique. The second regions are adapted to support a portion of the sample material disposed in the corresponding sample location and are sufficiently transparent or sufficiently non-interfering to a second form of radiation to permit analysis of a portion of the sample supported in the second region using the second analytical technique. The second regions are insufficiently transparent to the first form of radiation to permit analysis of the portion of the sample material supported in the second region using the first analytical technique.

In general, in a related aspect, the methods include providing a substrate having a first surface, a second surface, and a plurality of sample locations, irradiating the second surface of the substrate at a first region of one or more of the sample locations with a first form of radiation, detecting radiation transmitted through, emitted by or scattered by a corresponding sample material resulting from the irradiating at the first region, irradiating the second surface of the substrate at a second region of the one or more of the sample locations with a second form of radiation, and detecting radiation transmitted through, emitted by or scattered by the corresponding sample material resulting from the irradiating at the second region. The first region comprises a first substrate material and the second region comprises a second substrate material.

Particular embodiments can include one or more of the following features. The first form of radiation and the second form of radiation can be different forms of radiation selected from the group including x-ray radiation, IR radiation, UV-vis radiation, and visible radiation. The first analytical technique and the second analytical technique can be independently selected from (1) x-ray diffraction in a transmission geometry, (2) IR spectroscopy, and (3) UV-vis spectroscopy, Raman spectroscopy, fluorometry, polarimetry, or optical microscopy. The first regions can be transparent to x-ray radiation and comprise a material selected from the group consisting of beryllium, aluminum, polyimide, polyacetate, and polyethylene terephthalate. The second regions can be transparent to IR radiation and comprise a material selected from the group consisting of $BaF_2$, $CaF_2$, KBr and sodium chloride. Alternatively, the first regions can be transparent to IR radiation and comprise a material selected from the group consisting of $BaF_2$, $CaF_2$, KBr and sodium chloride. Where the first regions are transparent to x-ray radiation or IR radiation, the second regions can be optically transparent and comprise a material selected from the group consisting of glass, quartz and sapphire. The first regions can be transparent to x-ray radiation and comprise beryllium, and the second regions can be optically transparent and comprise glass, quartz or sapphire.

Providing the plurality of materials can include preparing each of the plurality of materials at the corresponding sample location of the substrate. Preparing each of the plurality of materials can include delivering one or more components to each of the plurality of sample locations, and transforming the one or more components to generate the plurality of materials. Transforming the one or more components can include one or more of exposing the one or more components to one or more environmental conditions and allowing the one or more components to react in the sample locations. Delivering one or more components can include delivering a plurality of solutions containing the one or more components to a plurality of samples wells of a sample holder assembly. The sample holder assembly can include the substrate and a substrate block. The substrate block can have a first surface and a second surface and include a plurality of through-holes extending from the first surface to the second surface. Each of the plurality of through-holes can correspond to one of the plurality of sample locations on the substrate. The substrate block can be releasably coupled to the substrate to form a plurality of sample wells. Each sample well can be formed from one of the sample locations and the corresponding through-hole. Transforming the one or more components can include generating one or more solid forms of the materials in the sample wells. The substrate block can be separated from the substrate before performing at least one of the screening steps.

In general, in still another aspect, the invention provides apparatus for holding samples for analysis. The apparatus includes a substrate having a plurality of sample locations for supporting a plurality of samples. Each of the plurality of sample locations provides a sample surface including a first region and a second region. Each of the first regions comprises a first substrate material sufficiently transparent or sufficiently non-interfering to a first form of radiation to permit analysis of a portion of a sample supported in the first region using an analytical technique selected from the group consisting of an x-ray technique, an infrared technique and a UV-Vis technique. The x-ray technique is x-ray diffraction in a transmission geometry. The infrared technique is an IR spectroscopy or thermal imaging technique. The UV-Vis technique is UV-vis spectroscopy, Raman spectroscopy, fluorometry, polarimetry, or optical microscopy. Each of the second regions comprises a second material sufficiently transparent to a second form of radiation to permit analysis of a portion of the sample supported in the second region using a different analytical technique selected from the group consisting of the x-ray technique, the infrared technique and the UV-Vis technique.

The invention can be implemented to realize one or more of the following advantages, alone or in the various possible combinations. Different regions of a single sample location can be used to perform multiple analytical measurements on a single sample. A first region can be used to perform a first type of analytical measurement, while a second region can be used to perform a second type of analytical measurement that cannot be performed (e.g., will not provide useful or meaningful results) if performed in the first region. Thus, analytical techniques having different requirements (e.g., as to substrate materials) can be performed on a sample or set of samples on a single substrate. For example, a sample material can be screened at a single sample location in a library using transmission x-ray diffraction analysis and one or more other screening techniques that require a substrate that is transparent to optical, ultraviolet, or infrared radiation. The performance of multiple analytical measurements on a sample minimizes the amount of handling of sample materials required to complete the screens. Multiple screens can be performed on a sample material without requiring transfer of the material to different substrates for the different screens. Sample materials can be prepared, stored, and screened on a single substrate. Sample materials can be prepared and/or screened in a variety of forms, including solids, liquids, solutions, suspensions, dispersions, emulsions, films, and gases. Sample materials can be prepared and screened under controlled environmental conditions.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
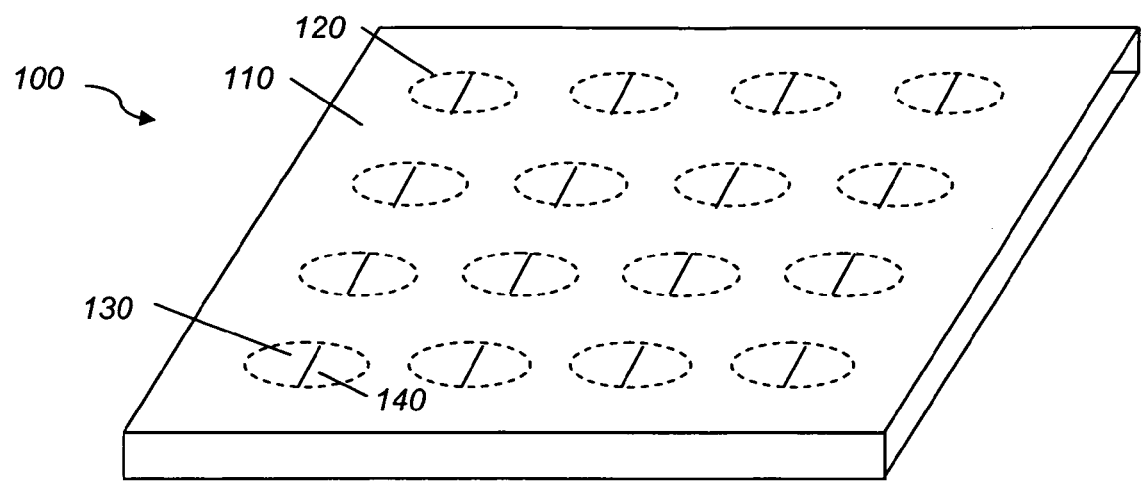
FIG. 1 is a diagram illustrating a sample holder assembly according to with one aspect of the invention.

The invention provides sample holder assemblies that can be used to perform multiple analyses on materials supported on the substrate. As illustrated in FIG. 1, a sample holder assembly 100 includes a substrate 110 with one or more sample locations 120 that are or can be configured to receive a sample material as will be described in more detail below. It should be noted that in some places in this specification, "sample holder assembly" refers to a device that incorporates one or more substrates for supporting sample materials, while in other places the substrate (or combination of substrates) is the sample holder assembly. Thus, the terms "substrate" and "sample holder assembly" can be synonymous, and can refer to a single, integral article or a combination of articles.

In the illustrated embodiment, each sample location includes two or more regions 130, 140. At least one of the regions is an x-ray transparent region 130, while at least one other region is an x-ray opaque region 140. The sample holder assemblies and substrates according to the invention can be used to perform multiple screening techniques upon sample materials disposed in the sample locations—specifically, to perform x-ray powder diffraction analysis in a transmission geometry upon the portion of the sample materials disposed in the x-ray transparent regions of the sample locations, and to perform one or more other screening techniques upon the portion of the sample materials disposed in the x-ray opaque regions, as will be discussed in more detail below.

In general, the substrate (or the sample holder assembly) is a structure having a rigid or semi-rigid surface. In many embodiments at least one surface of the substrate will be substantially flat. In some embodiments the substrate will contain physical separations between sample locations, as discussed in more detail below. Subject to the requirements of the analytical techniques and the material requirements of the x-ray transparent and x-ray opaque regions discussed below, the substrate can incorporate a variety of different materials, such as polymers, plastics, pyrex, quartz, resins, silicon, silica or silica-based materials, carbon, metals, inorganic glasses, inorganic crystals, and membranes. In particular embodiments, the substrate is at least partially formed from one or more organic polymers, beryllium, or aluminum. Surfaces on the substrate can be composed of the same materials as the substrate or of different materials—for example, the substrate can be coated with a different material. The particular choice of a material or materials for the substrate and any coatings can depend on the particular application.

Preferably, any surface of the substrate should exhibit chemical and mechanical stability to conditions to which it is likely to be exposed. For example, the surfaces upon which sample materials will be deposited or otherwise provided should be inert to the sample materials and, in some embodiments, the components from which they are prepared. The substrate can be formed in any desired shape—e.g., disc, square, rectangular—and in any desired size, subject to any limitations imposed by any chemistry to be performed on or screening techniques to be applied to the sample materials. Similarly, the size and dimensions of the substrate will depend upon the requirements of a particular application. In typical embodiments, the surface area of the substrate will be in the range of 1 $cm^2$ to 400 $cm^2$, although substrates having smaller or larger surface areas can be used.

Sample locations are provided on the substrate surface, and are generally localized area on the substrate that are, were, or are intended to be used to receive a sample material. In the following description, sample locations may be referred to, in the alternative, as "selected locations", or simply as "locations". The sample locations can have any convenient shape, such as linear, circular, rectangular, elliptical, or wedge-shaped, and can be arranged in any convenient configuration, such as a square, rectangular, circular or triangular array. As noted above, sample location boundaries can be defined on the substrate surface by physical separations. Suitable physical separations can include, for example, optical features, such as lines or other markings, or topographic features, such as dimples, wells, raised ridges or etched troughs. In other embodiments, small beads or pellets may be provided on the surface, either alone or within substrate surface dimples. Individual sample locations can be provided in any convenient shape—such as circles, squares, and the like. The area of the sample locations depends on the application and in typical embodiments is smaller than about 25 $cm^2$. However, in particular embodiments the sample locations can be smaller than 10 $cm^2$, smaller than 5 $cm^2$, smaller than 1 $cm^2$, smaller than 1 $mm^2$, smaller than 0.5 $mm^2$, smaller than 10,000 $\mu m^2$, smaller than 1,000 $\mu m^2$, smaller than 100 $\mu m^2$, or even smaller than 10 $\mu m^2$.

As noted above and as illustrated in FIG. 1, one or more of the sample locations on the substrate includes at least two regions. A first region of the one or more sample locations is adapted to permit the analysis of a sample material disposed in the respective sample location using a first analytical technique. Specifically, the substrate has one or more properties in the first region that adapt the substrate in that region for analyses using the first analytical technique. By contrast, the first analytical technique cannot usefully be performed in the second region. That is, the second region is not adapted to permit the analysis of the sample material disposed on the sample location using the first analytical technique, again because of one or more properties of the substrate in the second region.

The first analytical technique is a technique based on irradiation of sample materials disposed in the respective sample location or locations from one side of the substrate and subsequent detection of radiation on the opposite side of the substrate—for example, radiation transmitted through, emitted by or scattered by the sample material as in optical polarimetry, UV-Vis absorption spectroscopy, fluorometry, IR spectroscopy, Raman spectroscopy, or transmission x-ray diffraction. To facilitate use of the first analytical technique, the first region is transparent or sufficiently non-interfering to the radiation used in the first analytical technique. As used in this specification, a substrate region is transparent to a given form of radiation if the substrate in that region has the property of transmitting the particular electromagnetic radiation without appreciable absorption or scattering. As used in this context, absorption or scattering is appreciable if it impedes the detection of the corresponding sample material by the detection system. Thus, a substrate region that absorbs, emits or scatters incident electromagnetic radiation at a sufficiently low level (or at sufficiently different angles from the sample in the case of an x-ray diffraction system) that radiation emitted or scattered by the sample can be resolved by the detection system is transparent to that electromagnetic radiation for the purposes of this specification. As used in this specification, a substrate region is opaque to a given form of radiation if it is not transparent to that radiation—that is, if the substrate region absorbs, emits and/or scatters incident radiation in a transmission geometry at levels sufficient to interfere with the analysis (i.e., where the analysis is substantially influenced by the presence of the substrate).

In some embodiments, the first analytical technique is transmission x-ray powder diffraction and the substrate is transparent to x-rays in the first region or regions. In specific embodiments, the first region or regions are x-ray transparent if the intensity of the x-ray beam transmitted through the region is at least 50% of the intensity of the x-ray source, and the intensity of diffraction pattern produced by the substrate is less than 10% of the intensity of the diffraction pattern produced by the sample. In some such embodiments, the substrate in the first region or regions comprises one or more x-ray transparent materials. X-ray transparent materials that can be used in particular embodiments of the present invention include elements of small atomic number such as beryllium or aluminum that have small X-ray diffraction cross-sections, or amorphous materials such as polyimide (e.g., Kapton® Polyimide Film, available from DuPont High Performance Materials of Circleville, Ohio), polyacetate, and polyethylene terephthalate (e.g., Mylar® Polyester Film, available from DuPont Teijin Films, of Hopewell, Va.). The choice of particular x-ray transparent material or materials to be used to form x-ray transparent substrate regions in a particular embodiment will depend on the application.

In other embodiments, the first analytical technique is another analytical technique involving the transmission of incident radiation through the substrate and sample material, such as IR, UV-vis or Raman spectroscopy, or an optical technique such as fluorometry, polarimetry and/or optical microscopy, and the substrate is transparent to IR, UV or optical light in the first region. In some such embodiments, the substrate in the first region or regions comprises one or more materials transparent to the appropriate form of radiation. Those skilled in the art will recognize a variety of materials that are transparent to such radiation—such as $BaF_2$, $CaF_2$, KBr and sodium chloride for IR techniques, and glass, quartz and optically-transparent sapphire for UV-vis and/or optical techniques. Again, the choice of a material or materials will depend upon the particular application.

In some embodiments, the second region is adapted to permit the analysis of the sample material disposed in a given sample location using a second analytical technique. That is, as in the first region the substrate has one or more properties in the second region that adapt the substrate in that region for analyses using the second analytical technique. In particular embodiments, the second analytical technique cannot usefully be performed in the first region. Thus, for example, in some embodiments the first region is formed from an x-ray transparent material and is thus adapted for analysis of sample materials using x-ray powder diffraction, and the second region is formed from one or more substrate materials that would produce substantial diffraction in a transmission geometry, but that have some property or properties that is or are desirable in another screening technique to be applied to the sample materials. Exemplary materials that can be used in some such embodiments optically transparent materials such as glass, quartz, optically transparent sapphire, that can be used for transmission microscopy, birefringence, UV-visible, Raman, or fluorescence measurements, IR transparent material such as $BaF_2$, $CaF_2$, and sodium chloride, that can be used for transmission-based infrared screening techniques, and non-optically or IR transparent materials such as silicon, ceramics, and metals, that can be used for reflection-based screens. Particular useful combinations (i.e., first and second regions) can include, for example, x-ray transparent regions and IR transparent regions, x-ray transparent regions and UV-vis/Raman/optical transparent regions, and IR transparent regions and UV-vis/Raman/optical transparent regions. The choice of particular materials to be used to form the second regions will depend on the application—in particular, on the type of screening technique to be used.

The particular dimensions of the first regions and/or second regions will depend on the particular application. In typical embodiments, the surface area of these regions may be smaller than about 12 $cm^2$, smaller than 5 $cm^2$, smaller than 2.5 $cm^2$, smaller than 0.5 $cm^2$, smaller than 0.5 $mm^2$, smaller than 0.25 $mm^2$, smaller than 5,000 $\mu m^2$, smaller than 500 $\mu m^2$, smaller than 50 $\mu m^2$, or even smaller than 5 $\mu m^2$. In particular embodiments, each region should be thick enough to withstand the loads likely to be placed upon the substrate in that region (e.g., during the synthesis and/or screening processes). Thickness may also be dictated by the transparency requirements of the region—that is, for some materials thickness may be limited by the energy absorption, emission and/or scattering characteristics of the substrate material.

Optionally, the first and/or second regions can be coated with a thin layer of a different material. Such coatings can be useful to provide a consistent surface and/or environment in each sample location. In some cases, such as where the sample material is prepared by depositing components in the sample locations and transforming them under reaction conditions, the transformation of the components can be influenced by the chemical or physical characteristics of the surface upon which they are deposited. Providing a single, consistent surface in each sample location can help to ensure, for example, that the portion of a sample material prepared or deposited in the first region of a given sample location will experience the same conditions as the portion of the material prepared or deposited in the second region of that location. In some embodiments, the coating can be a thin layer of glass or other inert material. In such embodiments, the coating material should be selected and prepared so that it will not interfere with the intended use of the underlying first and/or second regions in any screening performed on the sample locations.

Figure 2A:
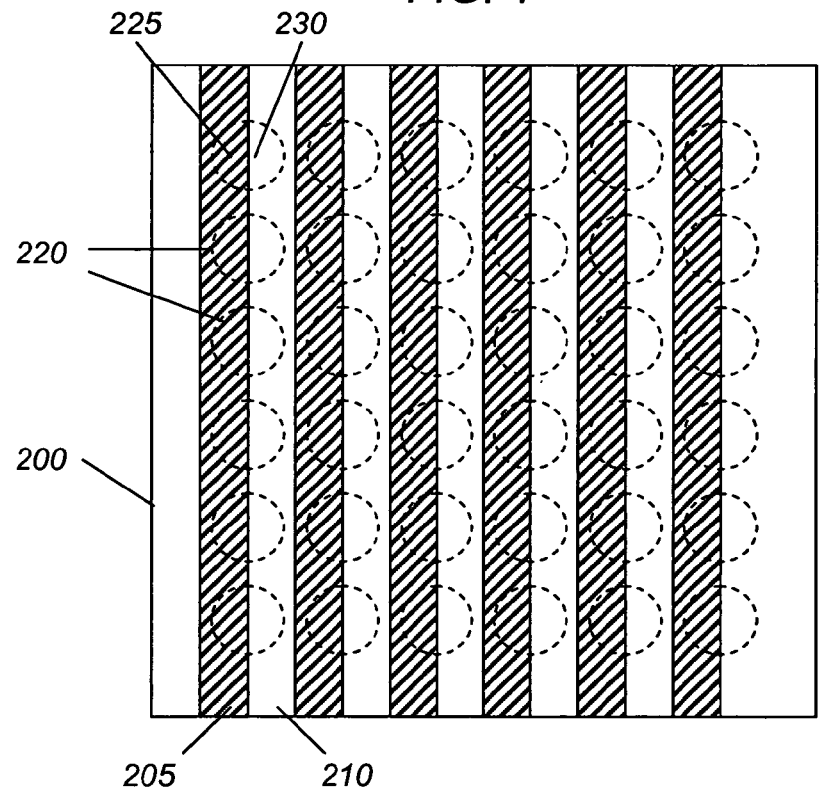
FIGS. 2A-2D are diagrams illustrating various embodiments of sample holder assemblies according to the invention.
Figure 2B:
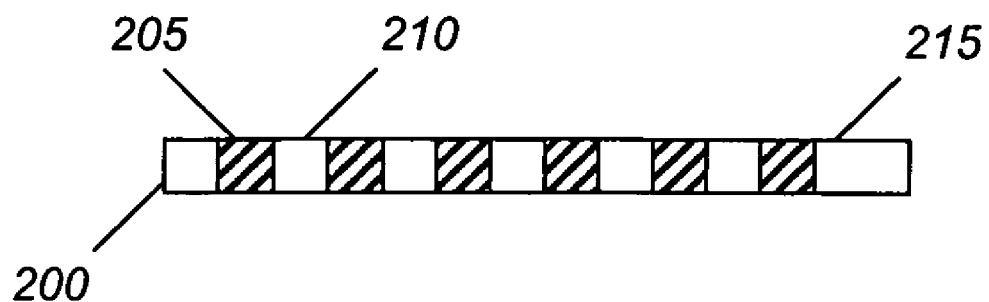
Figure 2C:
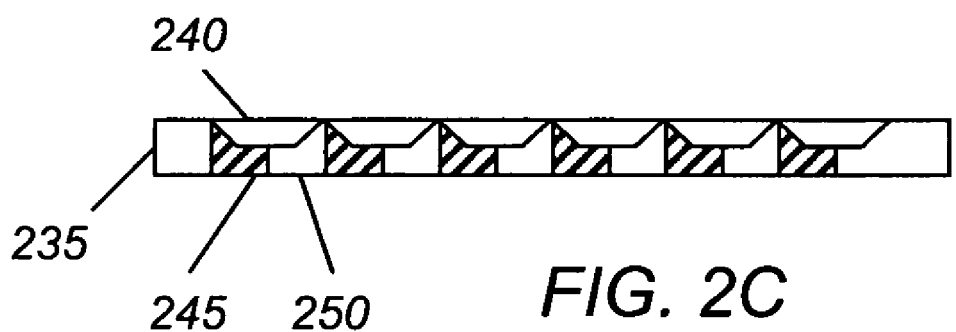

As noted above, the substrate provides a surface or surfaces upon which one or more sample materials can be provided. In particular embodiments, substrates can provide any convenient number of sample locations, such as 24 locations, 48 locations, 96 locations, 384 locations, or more. A number of embodiments directed to substrates useful for transmission x-ray diffraction analyses will now be described, although those skilled in the art will recognize that the same techniques and structures can be readily adapted to provide substrates for the other techniques (such as UV-vis, IR, Raman, birefringence, etc.) mentioned herein. In some embodiments, the substrate provides a single, substantially continuous surface for forming sample locations. In one such embodiment, illustrated in FIGS. 2A and 2B, a substrate 200 includes alternating x-ray transparent segments 205 and x-ray opaque segments 210 are joined together to form a single flat surface 215, and sample locations 220 are defined as a 6×6 array circular areas each of which includes a semicircular section 225 of one of the x-ray transparent segments (thus forming the first region of the sample location) and a semicircular section 230 of an adjacent x-ray opaque segment (forming the corresponding second region of the location). A similar embodiment is shown in FIG. 2C, in which substrate 235 includes an array of dimples 240 that define the sample locations, again each including an x-ray transparent portion 245 and an x-ray opaque portion 250.

Figure 2D:
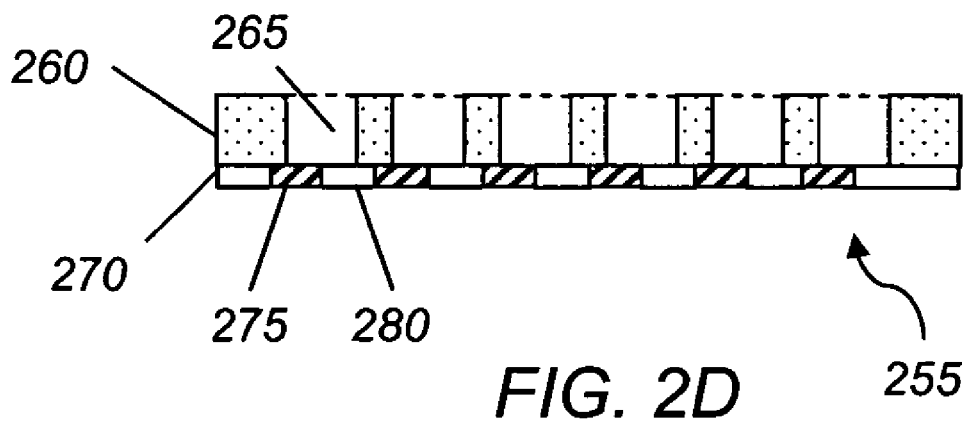
Figure 7A:
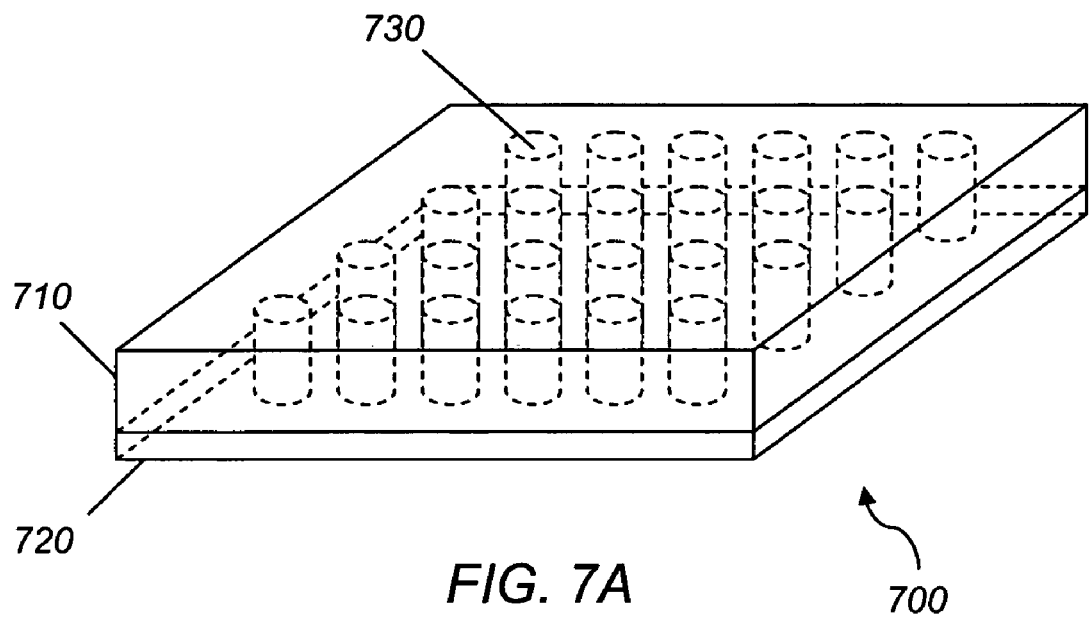
FIGS. 7A-7B are diagrams further illustrating another embodiment of a sample holder assembly according to the invention.
Figure 7B:
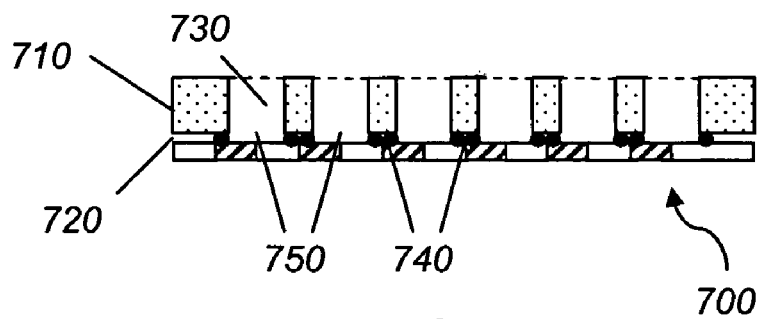

In other embodiments, the substrate surface can be discontinuous. In one such embodiment, illustrated in FIG. 2D, a substrate 255 includes a substrate block 260 that includes an array of channels 265. A base plate 270, which includes x-ray transparent portions 275 and x-ray opaque portions 280, is coupled or bonded to the base of substrate block 260 to define an array of wells in channels 265. In particular embodiments, plate 270 can be fixedly bonded to the base of substrate block 260. Alternatively, plate 270 can be removeable from block 260—for example, to facilitate cleaning or subsequent screening, as will be described in more detail below in the context of FIG. 7. In some embodiments, plate 270 can comprise alternating x-ray transparent and x-ray opaque segments, as shown for substrate 200 in FIGS. 2A and 2B above.

Figure 3:
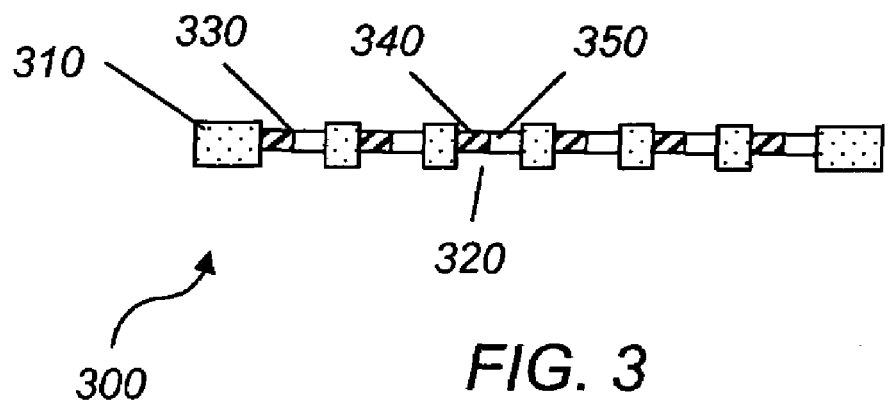
FIG. 3 is a diagram illustrating another embodiment of a sample holder assembly according to the invention.

In still another embodiment, illustrated in FIG. 3, a sample holder assembly 300 includes a substrate plate 310 that includes an array of-holes 320, each of which includes an insert 330 that comprises an x-ray transparent region 340 and an x-ray opaque region 350. In the embodiment shown in FIG. 3, inserts 330 are provided at or near the upper surface 360 of substrate plate 310, such that substrate 300 presents a substantially planar topography similar to substrate 200 (or base plate 270) discussed above. Alternatively, inserts 330 can be provided deeper within holes 320 (for example, where substrate 300 is deep relative to the diameter (or width) of holes 320, such that substrate 300 includes dimples or wells, similar to substrates 235 and 255, also discussed above. In some embodiments, inserts 330 can be fixed in place in substrate plate 310; alternatively, inserts 330 can be removeable.

In some embodiments in which the substrate provides a substantially planar surface (e.g., substrate 200), sample locations can be defined by etching a trench or trough in the upper surface of the substrate around each sample location. Alternatively, sample locations can be defined on the substrate surface during a sample material preparation phase by applying an external mask, form or template to the substrate surface. Thus, for example, a mask in such an embodiment can take the form of a thin sheet of rubber (e.g., a gasket) including an array of holes, where the rubber sheet can be superimposed on an underlying substrate surface to define a sample location in each of the holes.

Figure 4A:
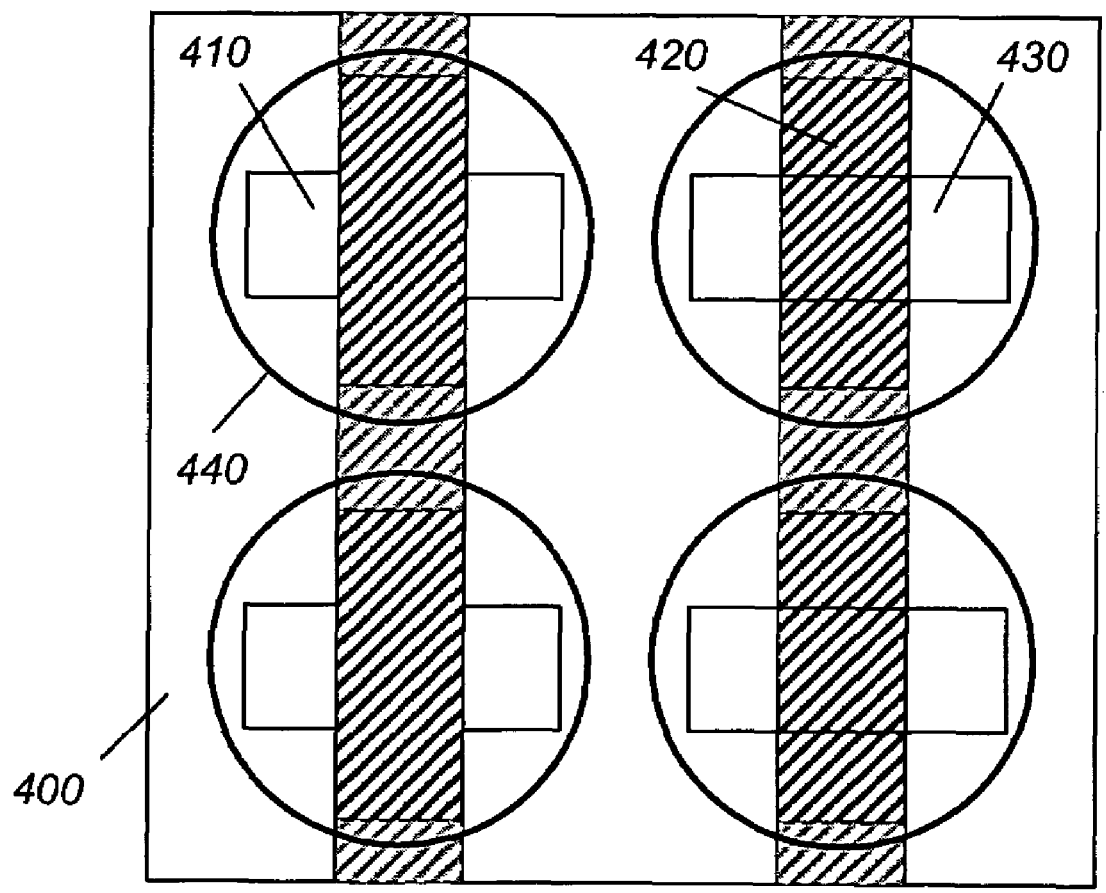
FIGS. 4A-4C are diagrams illustrating still another embodiment of a sample holder assembly according to the invention.
Figure 4B:
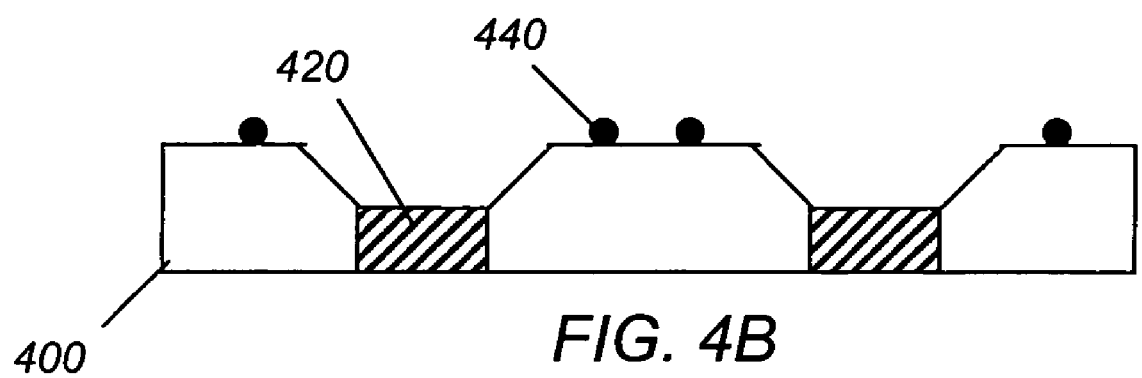
Figure 4C:
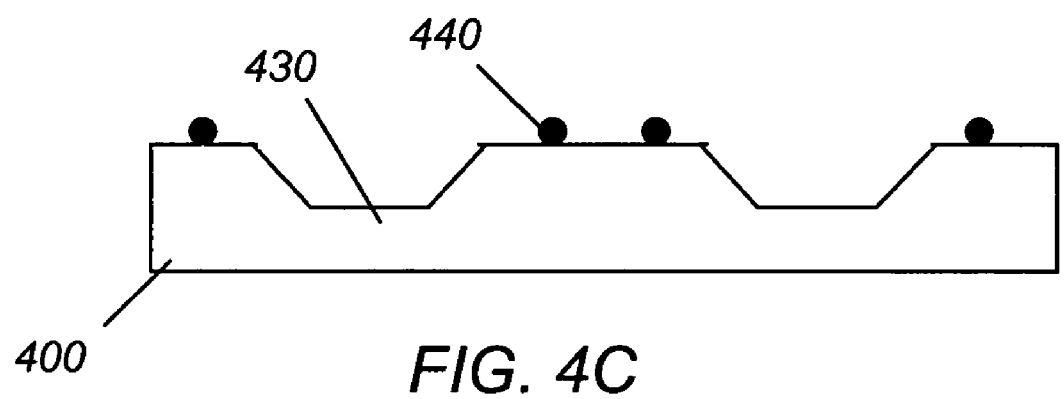

In other embodiments, where the substrate surface features dimples or depressions as illustrated in FIG. 2C, the appropriate surface features can be formed by machining, molding or shaping individual segments of materials from which the substrate will be fabricated, or by etching the surface of the fabricated substrate to define the respective dimples or depressions. One such embodiment is illustrated in FIG. 4A, where a sample holder assembly 400 includes a plurality of sample locations 410. As in substrate 200 discussed above, assembly 400 comprises alternating x-ray transparent segments 420 and x-ray opaque segments 430. Each sample location 410 is defined as a cruciform trough formed (e.g., etched) in the upper surface of substrate 400, as is illustrated more clearly in the sections shown in FIGS. 4B and 4C. In this embodiment, each sample location 410 is isolated from its neighbors with a circular o-ring or gasket 440, which may reside in a circular channel etched in the upper surface of substrate 400. This configuration can advantageously provide a liquid- and gas-tight seal around each sample location where substrate 400 is used as a base plate in embodiments such as that shown in FIG. 2D.

In general, substrates according to the invention can be prepared using known techniques. When the substrate comprises a plate of alternating segments of different materials (e.g., substrate 200 in FIG. 2A above), strips of the respective materials can be prepared (including optional molding or machining to provide any desired features, such as dimples, wells, or ridges to define the sample locations, or joints for subsequent bonding) and bonded or fused together using known techniques, such as anodic bonding, eutectic bonding, melt fusing, welding, epoxy, or the like. Alternatively, one set of strips can be prepared and embedded in the material that will form the other set—for example, to prepare a substrate comprising a square plate made up of alternating strips of beryllium and glass, a set of beryllium strips can be prepared and laid out in parallel in a square form. Molten glass can be introduced into the form and allowed to fill in the spaces between the beryllium strips. Optionally, the glass can be introduced into the form in an amount sufficient to both fill in these spaces and to cover the beryllium strips to a predetermined depth. Excess glass can then be removed—for example by etching—to provide a planar substrate with alternating strips of beryllium and glass available to provide x-ray transparent and x-ray opaque regions for sample locations distributed across the substrate, such as in a square planar array. Films or foils can be prepared by alternately depositing x-ray transparent and x-ray opaque materials upon a backing plate, which can be removed after the deposited materials are bonded together to form a sheet or other desired configuration. Similarly, when the substrate comprises an array of sample location inserts as illustrated in FIG. 3, individual inserts (which may be removeable/replaceable or fixed as described above) can be fabricated using analogous techniques.

As noted, the substrate can be used to perform multiple analyses of sample materials located at sample locations on the substrate. In general, as used herein a sample material is a substance or combination of substances that has been deposited onto a sample location of a substrate for screening. The sample materials can include a single component, or a combination of components that have reacted directly with each other or with an external source. Alternatively, the sample materials may include a layer, blend or mixture of components in a sample location of the substrate. A component, as that term is used herein, is an individual substance—an element, a chemical, a material, or a mixture of elements and chemicals—that has been or will be deposited onto a substrate. Components can act upon (e.g., react with) one another to produce a particular sample material. Alternatively, a component or components can form sample materials upon exposure to or interaction with an external condition, such as exposure to an energy source such as radiation, an electric field, a magnetic field, or a third material or a chemical substance that acts upon the component or components. Exemplary sample materials that can be provided in particular embodiments include, but are not limited to, covalent network solids, ionic solids and molecular, inorganic materials, intermetallic materials, metal alloys, ceramic materials, organic materials, organometallic materials, organic polymers, composite materials (e.g., inorganic composites, organic composites, or combinations thereof), and homogeneous or heterogeneous catalysts.

Thus, an array of sample materials is prepared by providing sample materials sample locations on the substrate. In a typical embodiment, an array of materials is prepared by successively delivering components of the materials to different sample locations on a substrate, and allowing the components interact (e.g., react) to form at least two materials at the different sample locations. Thus, for example, a first component of a first material can be delivered to a first sample location, and a first component of a second material delivered to a second sample location on the same substrate. A second component of the first material can then be delivered to the first sample location, and a second component of the second material delivered to the second sample location. In particular embodiments, the components can be delivered in solid, liquid, or gaseous form—for example, as crystalline solids, powders, amorphous solids, liquids, solutions, slurries, emulsions, dispersions, films, or the like. The components can be delivered in a uniform or gradient fashion where appropriate, to produce either a single stoichiometry or, alternatively, a large number of stoichiometries within a single sample location. The process is repeated, with additional components, to form an array of components at predefined sample locations on the substrate. The components can be delivered in any convenient quantities—for example, in milligram-, microgram-, nanogram-, or even picogram-scale amounts. The particular amount of any given component will be determined based on the particular application, although in many embodiments it can be advantageous to use as little material as possible.

Thereafter, the components are allowed to interact to form at least two materials at their respective sample locations. The components can interact to form layers, blends, mixtures, and/or materials resulting from a reaction between components. In some embodiments, for example, the components can be reacted using techniques such as solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent or cooling, precipitation with an anti-solvent, etc. Furthermore, in some embodiments sample locations can be heated (or cooled) simultaneously or sequentially using heat sources such as focused infrared radiation, resistive heating, etc. Additionally, in some embodiments components can react with each other instantly, upon contacting each other, including in the air before contacting the substrate.

The components can be sequentially or simultaneously delivered to the sample locations on the substrate using any of a number of different delivery techniques, including, for example, manual, automated, or semi-automated liquid- and/or powder-dispensing techniques, chemical or physical vapor deposition, or the like. The choice of particular techniques for delivering components to the sample locations will depend on a number of factors, including the chemical and physical properties of the components and desired sample materials, the configuration of the substrate, and any processing (e.g., reaction conditions) that will be applied to the components and/or sample materials on the substrate. Ultimately, each sample material is provided such that the sample material is present in both the x-ray transparent region and the x-ray opaque region of its respective sample location, as will also be discussed below.

When the array of sample materials has been prepared, the substrate is subjected to multiple different analytical screens to obtain information about the materials provided in the sample locations. In some embodiments, the entire array (i.e., each sample location on the substrate) is subjected to the screen; alternatively, a section of the substrate (e.g., a selected row of sample locations, or set of selected individual sample locations) can be screened. In either case, the sample locations can be screened sequentially, preferably using fast sequential screening, or in parallel.

Figure 5:
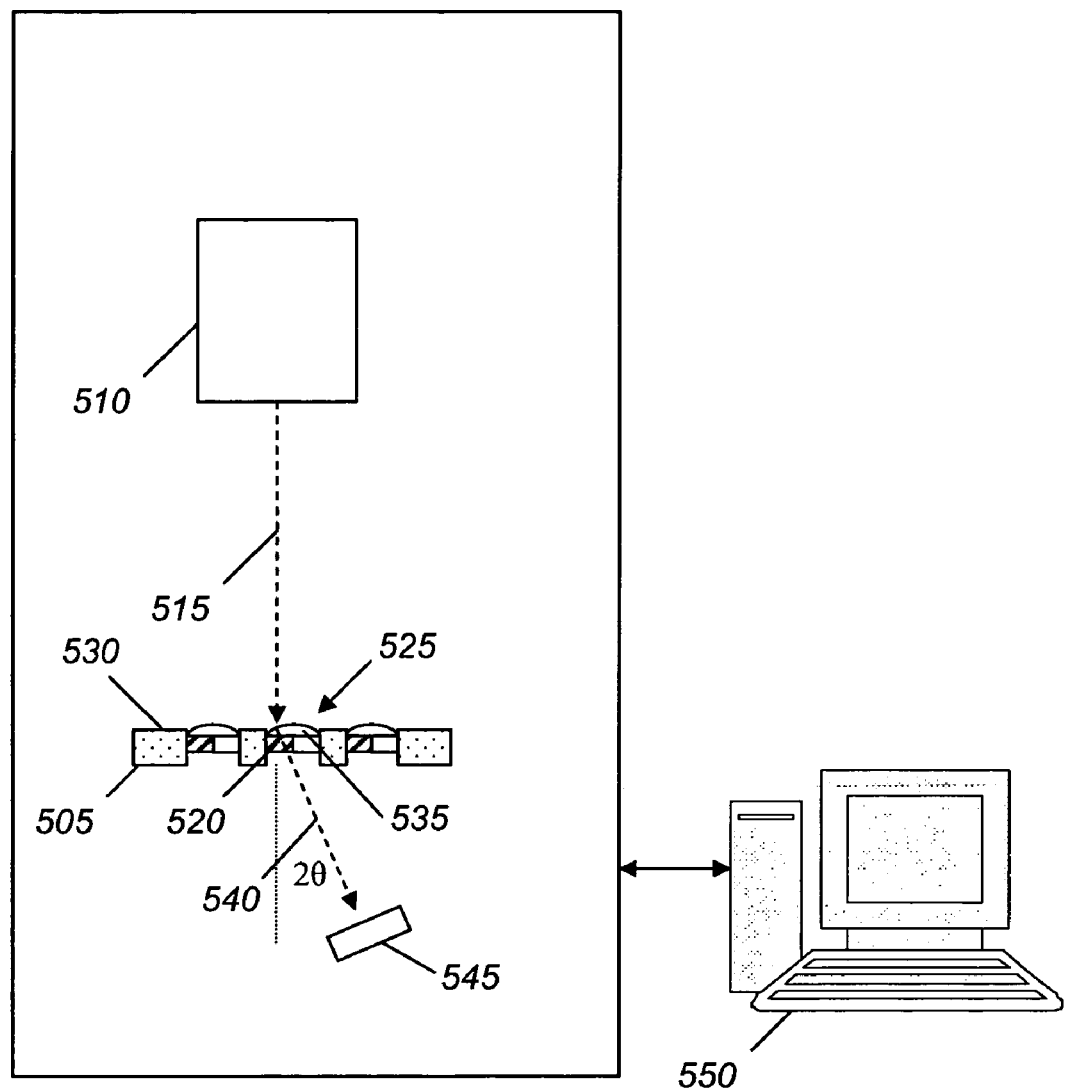
FIG. 5 is a block diagram illustrating an x-ray characterization apparatus for configured to perform transmission x-ray diffraction analysis on sample locations of a sample holder assembly according to one aspect of the invention.

In one embodiment, a sample material or materials are screened in a first screen using x-ray diffraction in a transmission geometry, illustrated for an x-ray diffraction system 500 in FIG. 5. In this screen, the substrate 505 is positioned in diffractometer 500 to align x-ray source 510 so that a beam of x-ray radiation 515 will strike the x-ray transparent region 520 of a particular sample location 525 in an orientation that is approximately perpendicular to the substrate surface 530. The x-ray beam 515 strikes the sample material 535 in the x-ray transparent region 520, and is diffracted through an angle 2θ as it passes through the sample material 535. Because x-rays 515 strike material 535 in x-ray transparent region 520, they do not interact, or only minimally interact, with substrate 505 as they pass through the substrate. The diffracted x-rays 540 are detected at detector 545, which produces a signal indicative of the intensity of the detected diffracted x-ray beam 540. The signal is provided to computer 550, which processes the signal to generate a conventional x-ray diffractogram indicating the intensity and 2θ values for the various signals detected for sample material 535. It should be noted that while FIG. 5 shows x-ray source 510 located above (i.e., on the sample side of) substrate 505 and detector 545 located below substrate 505, diffractometer 500 can be configured to introduce the x-ray beam from the opposite orientation—that is, from below the substrate, so that the x-rays pass through the substrate before interacting with the sample materials and continuing to the detector. When the signal acquisition for sample material 535 is complete, the system proceeds to the next sample material on substrate 505—for example, by moving substrate 505 relative to x-ray source 510, or by moving x-ray source 510 relative to substrate 505, by a predetermined distance to align x-ray source 510 with the x-ray transparent region of another sample location. A suitable apparatus for performing x-ray diffraction screening in either transmission or reflection mode is described in more detail in U.S. Pat. No. 6,371,640, which is incorporated by reference herein.

In a second screen, a sample material or materials are screened using a different analytical screening technique, such as Raman spectroscopy, infrared spectroscopy, fluorometry, polarimetry, or optical microscopy, in which the relevant sample locations are exposed to electromagnetic radiation appropriate to the screening technique—for example, visible light in the case of optical microscopy, or infrared radiation in the case of IR spectroscopy or thermal imaging The electromagnetic radiation strikes the sample material or materials in the x-ray opaque region of the corresponding sample locations, interacts with the material, and resulting radiation is detected by an appropriately positioned detector and processed to provide the corresponding information (e.g., a Raman spectrum, IR spectrum, thermal image, optical image, or the like) about the screened material or materials. It should be noted that the second screen and x-ray opaque material(s) are selected so that the x-ray opaque material has no substantial effect on the performance of the second screen. Thus, in some embodiments the second screen and the x-ray opaque material are selected so that the electromagnetic radiation of the second screen is substantially free from interactions with the x-ray opaque material (e.g., so that the x-ray opaque material does not absorb, scatter or otherwise interact with the electromagnetic radiation, either before or after it interacts with the sample material in the x-ray opaque region). In some embodiments, the second screen involves the detection of radiation transmitted through the sample materials, such that the sample materials are irradiated from one side of the substrate, and radiation is detected on the other side of the substrate after having passed through and/or interacted with the sample materials and the substrate. In other embodiments, the second screen detects light reflected from the sample materials or substrate—that is, the radiation is introduced and detected from the same side of the substrate, as in reflection x-ray diffraction analysis. In either geometry, the second screen can detect radiation that results from any phenomenon, such as scattering of the incident radiation by the sample material, emission of radiation after absorption of the incident radiation by the sample material, or the like. In particular embodiments, the second screen may or may not be performed on the same sample materials analyzed in the first screen. In some embodiments, multiple second screens can be performed on some or all of the samples deposited on the substrate. The second screen or screens can be performed before or after the transmission x-ray diffraction (i.e., first) screen discussed above. By properly selecting the materials and configuration of the substrate and sample locations, it can be possible to perform any number of analytical screens on a collection of sample materials on a single substrate, without requiring the removal of the sample materials from the substrate.

The screens can be applied to measure a variety of different properties, such as electrical, thermal, mechanical, morphological, optical, chemical, anisotropy, crystallinity, optical transparency, birefringence, and other useful properties. Thus, x-ray diffraction analysis in either transmission or reflection geometry can be used to determine the presence and diffraction pattern of crystalline materials, to identify the presence of known crystalline phases present in solid materials and powders, and to determine the structural properties, such as stress, grain size, phase composition, crystal orientation, and defects, of the materials, as discussed, for example, in U.S. Pat. No. 6,371,640, which is incorporated by reference above. Infrared screening techniques can be used to monitor thermal properties, such as infrared absorbtion or reflectance, as described in U.S. Pat. No. 6,536,944, which is incorporated by reference herein. Optical techniques such as light scattering and birefringence can be used to screen for such properties as crystallinity, melting point, magnetization, coercivity, dielectric coefficient, and the like, as described in U.S. Pat. Nos. 6,157,449, 6,373,570, and U.S. Patent Application Publication No. US2003/0124028, all of which are incorporated by reference herein. In some embodiments, the sample materials may undergo chemical transformations (e.g., degradation, phase changes, or chemical reactions) while the screening is underway, or between the times when the first and second screens are performed.

Figure 6:
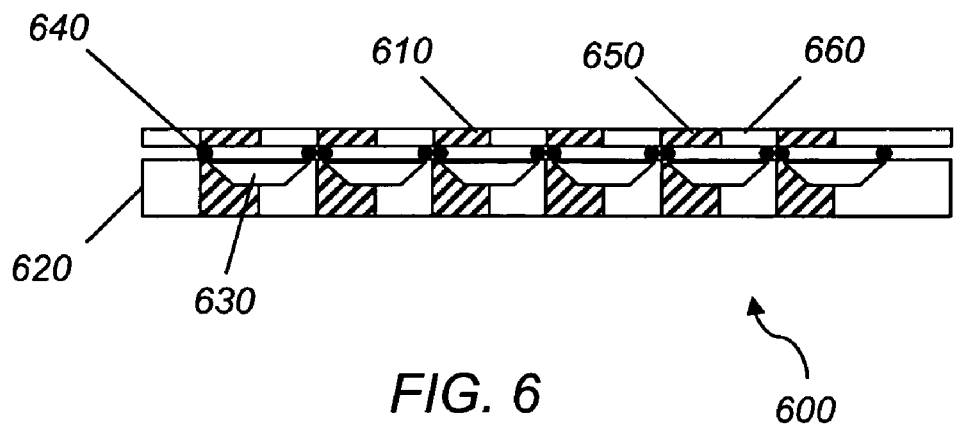
FIG. 6 is a diagram further illustrating one embodiment of a sample holder assembly according to the invention.

In some embodiments, it may be desirable to screen materials that are sensitive to environmental conditions, or that are not in solid form. To this end, in one aspect of the invention illustrated in FIG. 6, a sample holder assembly 600 is provided with a cover 610 that can be coupled with a substrate 620 to isolate individual sample locations 630 from each other and from the environment surrounding the substrate. In the embodiment illustrated in FIG. 6, sample locations 630 are provided as dimples or depressions in substrate 620. Each sample location 630 is provided with a sealing element 640, such as a gasket or o-ring, such that when cover 610 is coupled to substrate 620, for example, using securing bolts, an air- and liquid-tight seal is formed around each sample location. Optionally, cover 610 can be configured with pierceable seals (e.g., septa), so that a needle or cannula can be used to introduce components (e.g., liquids or gases) into sample locations 630. As shown in FIG. 6, cover 610 is configured with first regions 650 and second regions 660 that correspond to the first regions and second regions of substrate 620, so that when cover 610 is coupled to substrate 620, cover 610 does not absorb or otherwise interfere with the electromagnetic radiation used in the screens that will be applied to the sample materials in sample locations 630. In other embodiments, the cover need not include corresponding first and/or second regions, if it will be removed before the corresponding screen or screens will be performed. Preferably, the cover is formed from one or more materials that are impervious to air, water, and any chemical species that will be contained within the sample locations, and that are inert to the chemical and environmental conditions to which it will be exposed.

As noted above, the sample materials can be synthesized or prepared in their corresponding sample locations on the substrate before being subjected to the screens. For example, a component or components can be delivered to a sample location and then subjected to environmental conditions that cause a transformation to form the sample material. Similarly, two or more components can be delivered to a sample location and allowed to react to form the sample material. To this end, in one aspect of the invention illustrated in FIG. 7A, a sample holder assembly 700 includes a substrate block 710 that can be coupled to a base plate 720 to define a plurality of sample wells 730. In one embodiment, illustrated in FIG. 7B, sample holder assembly 700 includes a series or array of gaskets or o-rings 740 associated with sample locations 750, such that when substrate block 710 is coupled to base plate 720, a seal is formed that isolates each sample location 750 from each other sample location on the substrate. Optionally, sample holder assembly 700 can also include a cover that can be used to further seal sample wells 730 from each other and from the surrounding atmosphere, as described in the context of FIG. 6, above.

Sample wells 730 can be used as vessels for performing any chemistry necessary to synthesize or otherwise process the sample materials before (or during or after) screening. Thus, for example, individual components can be introduced into sample wells 730 using conventional techniques and allowed to react to form sample materials for subsequent screening. Similarly, solutions of different sample materials can be pipetted into sample wells 730 and subjected to crystallization conditions in order to produce solid forms of one or more of the sample materials for screening. Optionally, base plate 720 can then be separated from substrate block 710 (if necessary, after the removal of any residual solvent or the like), and can be subjected to screening as described above. Depending on the particular screens to be performed, in some embodiments it may be possible to perform one or more screens while substrate block 710 (and optionally, any cover as well) are still coupled to base plate 720. For example, infrared screening techniques can be used to monitor heat produced during reactions in sample wells 730.

Substrate block 710 can be formed from any material that is chemically and mechanically stable to the conditions to which it is likely to be exposed. In some embodiments, substrate block 710 is formed from aluminum, stainless steel, or organic polymers such as polyethylene. In some embodiments, metallic materials are preferred because of their thermal and mechanical properties. Moreover, in some embodiments substrate block 710 can be configured to subject sample wells 730 to a controlled thermal profile. For example, substrate block 710 can include channels that can be used to distribute a temperature-controlled fluid in proximity to sample wells 730. Optionally, if substrate block 710 is made from a material that is not sufficiently inert to the relevant chemistry, sample wells 730 can be lined with a chemically-inert material, such as polytetrafluoroethylene, to protect against corrosion or other chemical degradation of substrate block 710.

A number of embodiments of the invention have been described. Nevertheless, it will be understood that various modifications may be made without departing from the spirit and scope of the invention. For example, while the invention has been described in the context of embodiments in which each sample location on a substrate includes a first region and a second region, in some embodiments a substrate according to the invention can include one or more sample locations that do not include a first region, or that do not include a second region. Likewise, while the discussion above illustrates only embodiments having sample locations that include only a single first region and a single second region, in some embodiments substrates according to the invention can feature one or more sample locations that include multiple first regions and/or multiple second regions, where the different first and/or second regions may be composed of the same or different materials. Likewise, although the invention has been described in the context of embodiments involving sample locations having first and second regions and the use of first and second analytical techniques, it is contemplated that one or more sample locations may include additional (e.g., third) substrate regions, which may be incompatible with one or both of the first and second analytical techniques, and which may be adapted to permit the use of additional analytical techniques. Accordingly, other embodiments are within the scope of the following claims.

What is claimed is:

1. An apparatus for holding samples for analysis, the apparatus comprising:

a substrate having a surface providing a plurality of sample locations for receiving a plurality of samples, each sample location of the plurality of sample locations comprising a first region and a second region, the first region comprising a first material and the second region comprising a second material different from the first material, the first region being adapted to support a portion of a sample material disposed in the corresponding sample location, the first material of the first region being sufficiently transparent to a first form of radiation corresponding to a first wavelength range to permit analysis of the portion of the sample material supported in the first region using a first analytical technique, the second region being adapted to support a portion of the sample material disposed in the corresponding sample location, the second material of the second region being sufficiently opaque to the first form of radiation to prohibit analysis of the portion of the sample material supported in the second region using the first analytical technique, and the second material of the second region being sufficiently transparent to a second form of radiation corresponding to a second wavelength range different from the first wavelength range to permit analysis of the portion of the sample supported in the second region using a second analytical technique, the first material of the first region being sufficiently opaque to prohibit analysis of the portion of the sample material supported in the first region using the second analytical technique.

2. The apparatus of claim 1, wherein:

the first form of radiation and the second form of radiation are different forms of radiation selected from the group consisting of x-ray radiation, IR radiation, UV-Vis radiation, and visible radiation.

3. The apparatus of claim 2, wherein:

the first analytical technique and the second analytical technique are independently selected from (1) x-ray diffraction in a transmission geometry, (2) IR spectroscopy, and (3) UV-vis spectroscopy, Raman spectroscopy, fluorometry, polarimetry, or optical microscopy.

4. The apparatus of claim 1, wherein:

the substrate surface is a substantially flat surface, each sample location of the plurality of sample locations being provided as a separate location on the substantially flat surface.

5. The apparatus of claim 1, wherein:

the substrate includes a plurality of receptacles for receiving the plurality of samples, each sample location of the plurality of sample locations corresponding to one receptacle of the plurality of receptacles.

6. The apparatus of claim 1, wherein:

each sample location of the plurality of sample locations includes two or more second regions.

7. The apparatus of claim 1, wherein:

the substrate includes segments of the first material adjacent to segments of the second material, each sample location of the plurality of sample locations including at least a portion of one or more of the segments of the first material and at least a portion of one or more of the segments of the second material.

8. The apparatus of claim 1, wherein:

the substrate includes a plurality of removeable inserts, each removable insert of the plurality of removeable inserts providing a sample support surface for a corresponding one of the sample locations and including the first region and the second region of the corresponding sample location.

9. The apparatus of claim 8, wherein:

the substrate includes a substrate plate having a first surface and a second surface, the substrate plate defining a plurality of through-holes extending from the first surface to the second surface, each through-hole of the plurality of through-holes being configured to receive one insert of the plurality of inserts.

10. The apparatus of claim 8, wherein:

each removable insert of the plurality of removeable inserts includes a segment of the first material and a segment of the second material located adjacent to the segment of the first material.

11. The apparatus of claims 7 or 10, wherein:

each sample location of the plurality of sample locations has a sample support surface covering the corresponding portions of the segments of the first material and the second material to provide a uniform surface for receiving the sample material in the sample location.

12. The apparatus of claim 1, wherein:

the apparatus includes a sample support surface including a layer of material that does not substantially interfere with either the first analytical technique in the first region or the second analytical technique in the second region.

13. The apparatus of claim 12, wherein:

the first analytical technique is x-ray diffraction in a transmission geometry; and the sample support surface is formed from a layer of glass that is sufficiently thin to avoid substantial scattering of x-rays during the transmission x-ray diffraction analysis in the first region.

14. The apparatus of claim 1, further comprising:

a sealing layer configured to cover the sample locations, the sealing layer including a plurality of first regions and a plurality of second regions corresponding to the plurality of first regions and the plurality of second regions of the sample locations defined on the substrate surface.

15. The apparatus of claim 1, further comprising:

a substrate block having a first surface and a second surface, the substrate block including a plurality of through-holes extending from the first surface to the second surface, each through-hole of the plurality of through-holes corresponding to one sample location of the plurality of sample locations, the substrate block being configured to be releasably coupled to the substrate to form a plurality of sample wells, each sample well of the plurality of sample wells being formed by one of the sample locations and the corresponding through-hole.

16. The apparatus of claim 1, wherein:

the substrate surface provides at least 24 sample locations.

17. The apparatus of claim 1, wherein:

the substrate surface provides at least 48 sample locations.

18. The apparatus of claim 1, wherein:

the substrate surface provides at least 96 sample locations.

19. The apparatus of claim 1, wherein:

the substrate surface provides at least 384 sample locations.

20. The apparatus of claim 1, wherein:

the first regions are transparent to x-ray radiation and the first material is selected from the group consisting of beryllium, aluminum, polyimide, polyacetate, and polyethylene terephthalate.

21. The apparatus of claim 20, wherein:
the second regions are transparent to IR radiation and the second material is selected from the group consisting of $BaF_2$, $CaF_2$, KBr and sodium chloride.

22. The apparatus of claim 1, wherein:
the first regions are transparent to IR radiation and the first material is selected from the group consisting of $BaF_2$, $CaF_2$, KBr and sodium chloride.

23. The apparatus of claim 20 or 22, wherein:
the second regions are optically transparent and the second material is selected from the group consisting of glass, quartz and sapphire.

24. The apparatus of claim 1, wherein:
the first regions are transparent to x-ray radiation and the first material comprises beryllium; and
the second regions are optically transparent and the second material comprises glass, quartz or sapphire.

25. A method of screening a plurality of materials, the method comprising:
providing a plurality of sample materials in a corresponding plurality of separate sample locations on a substrate, each sample location of the plurality of sample locations comprising a first region and a second region, the first region comprising a first material and the second region comprising a second material different from the first material, the first region being adapted to support a portion of the sample material disposed in the corresponding sample location, the first material of the first region being sufficiently transparent to a first form of radiation corresponding to a first wavelength range to permit analysis of the portion of the sample material supported in the first region using a first analytical technique, the second region being adapted to support a portion of the sample material disposed in the corresponding sample location, the second material of the second region being sufficiently transparent to a second form of radiation corresponding to a second wavelength range different from the first wavelength range to permit analysis of a portion of the sample supported in the second region using a second analytical technique, the second material of the second region being sufficiently opaque to the first form of radiation to prohibit analysis of the portion of the sample material supported in the second region using the first analytical technique, and the first material of the first region being sufficiently opaque to the second form of radiation to prohibit analysis of the portion of the sample materials supported in the first region using the second analytical technique;
screening a first one of the plurality of sample materials at a first sample location of the substrate using the first analytical technique; and
screening the first one of the plurality of sample materials at the first sample location of the substrate using the second analytical technique.

26. The method of claim 25, wherein:
the first form of radiation and the second form of radiation are different forms of radiation selected from the group consisting of x-ray radiation, IR radiation, UV-vis radiation, and visible radiation.

27. The method of claim 26, wherein:
the first analytical technique and the second analytical technique are independently selected from (1) x-ray diffraction in a transmission geometry, (2) IR spectroscopy, and (3) UV-vis spectroscopy, Raman spectroscopy, fluorometry, polarimetry, or optical microscopy.

28. The method of claim 25, wherein:
the first region are transparent to x-ray radiation and the first material is selected from the group consisting of beryllium, aluminum, polyimide, polyacetate, and polyethylene terephthalate.

29. The method of claim 28, wherein:
the second regions are transparent to IR radiation and the second material is selected from the group consisting of $BaF_2$, $CaF_2$, KBr and sodium chloride.

30. The method of claim 25, wherein:
the first regions are transparent to IR radiation and the first material is selected from the group consisting of $BaF_2$, $CaF_2$, KBr and sodium chloride.

31. The method of claim 28 or 30, wherein:
the second regions are optically transparent and the second material is selected from the group consisting of glass, quartz and sapphire.

32. The method of claim 25, wherein:
the first regions are transparent to x-ray radiation and the first material comprises beryllium; and
the second regions are optically transparent and the second material comprises glass, quartz or sapphire.

33. The method of claim 25, wherein:
providing the plurality of sample materials includes preparing each sample material of the plurality of sample materials at the corresponding sample location of the substrate.

34. The method of claim 33, wherein:
preparing each sample material of the plurality of sample materials includes delivering one or more components to each sample location of the plurality of sample locations, and transforming the one or more components to generate the plurality of sample materials.

35. The method of claim 34, wherein:
transforming the one or more components includes one or more of exposing the one or more components to one or more environmental condition and allowing the one or more components to react in the sample location.

36. The method of claim 34, wherein:
delivering one or more components includes delivering a plurality of solutions containing the one or more components to a plurality of sample wells of a sample holder assembly, the sample holder assembly including the substrate and a substrate block, the substrate block having a first surface and a second surface and including a plurality of through-holes extending from the first surface to the second surface, each through-hole of the plurality of through-holes corresponding to one sample location of the plurality of sample locations on the substrate, the substrate block being releasably coupled to the substrate to form a plurality of sample wells, each sample well being formed from one of the sample locations and the corresponding through-hole; and
transforming the one or more components includes generating one or more solid forms of the sample materials in the sample wells;
the method further comprising separating the substrate block from the substrate before performing at least one of the screening steps.

37. A method of screening a plurality of materials, the method comprising:
providing a substrate having a first surface, a second surface, and a plurality of sample locations, each sample location of the plurality of sample locations comprising a first region and a second region, the first region comprising a first substrate material and the second region comprising a second substrate material different from the first substrate material, a plurality of sample materials being disposed on the first surface of the substrate in a corresponding plurality of the sample locations, the first substrate material being sufficiently transparent to a first form of radiation corresponding to a first wavelength range to permit screening by a first screening technique and being sufficiently opaque to a second form of radiation to prohibit screening by a second screening technique, and the second substrate material being sufficiently transparent to the second form of radiation corresponding to a second wavelength range different from the first wavelength range to permit screening by the second screening technique and being sufficiently opaque to the first form of radiation to prohibit screening by the first screening technique;

irradiating the second surface of the substrate at the first region of one or more of the sample locations with the first form of radiation;

detecting radiation transmitted through, emitted by or scattered by the corresponding sample material resulting from the irradiating at the first region;

irradiating the second surface of the substrate at the second region of the one or more of the sample locations with the second form of radiation; and detecting radiation transmitted through, emitted by or scattered by the corresponding sample material resulting from the irradiating at the second region.

38. An apparatus for holding samples for analysis, the apparatus comprising:

a substrate having a plurality of sample locations for supporting a plurality of samples, each sample location of the plurality of sample locations providing a sample surface including a first region and a second region, each first region comprising a first substrate material sufficiently transparent to a first form of radiation corresponding to a first wavelength range to permit analysis of a portion of a sample supported in the first region using a first analytical technique selected from a group consisting of an x-ray technique, an infrared technique and a UV-Vis technique, the x-ray technique being x-ray diffraction in a transmission geometry, the infrared technique being an IR spectroscopy or thermal imaging technique, and the UV-Vis technique being UV-vis spectroscopy, Raman spectroscopy, fluorometry, polarimetry, or optical microscopy, each second region comprising a second substrate material sufficiently transparent to a second form of radiation corresponding to a second wavelength range different from the first wavelength range to permit analysis of a portion of the sample supported in the second region using a second analytical technique selected from the group and different from the first analytical technique, the first substrate material being different from the second substrate material, the first substrate material being sufficiently opaque to the second form of radiation to prohibit analysis of the portion of the sample supported in the first region by the second analytical technique, and the second substrate material being sufficiently opaque to the first form of radiation to prohibit analysis of the portion of the sample supported in the second region by the first analytical technique.

* * * * *

UNITED STATES PATENT AND TRADEMARK OFFICE
CERTIFICATE OF CORRECTION

PATENT NO.        : 7,597,852 B2                                   Page 1 of 1
APPLICATION NO. : 11/219445
DATED             : October 6, 2009
INVENTOR(S)       : Desrosiers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1069 days.

Signed and Sealed this

Twenty-eighth Day of September, 2010

David J. Kappos
*Director of the United States Patent and Trademark Office*